(12) United States Patent
Danz et al.

(10) Patent No.: US 6,937,893 B2
(45) Date of Patent: Aug. 30, 2005

(54) PHYSICALLY ACTIVE PATCH, METHODS OF MANUFACTURING SAME AND ITS USE

(75) Inventors: Rudi Danz, Kleinmachnow (DE); Burkhard Elling, Potsdam (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 384 days.

(21) Appl. No.: 10/205,056

(22) Filed: Jul. 25, 2002

(65) Prior Publication Data
US 2003/0023270 A1 Jan. 30, 2003

(30) Foreign Application Priority Data
Jul. 26, 2001 (DE) ......................................... 101 36 402

(51) Int. Cl.[7] ................................................. A61N 1/18
(52) U.S. Cl. ......................................................... 607/3
(58) Field of Search ..................... 600/459; 310/313 R, 310/327; 128/904; 607/2, 3

(56) References Cited

U.S. PATENT DOCUMENTS

| | | | | |
|---|---|---|---|---|
| 4,549,107 A | * | 10/1985 | Kaneko et al. | 310/327 |
| 5,598,845 A | * | 2/1997 | Chandraratna et al. | 600/459 |
| 6,262,513 B1 | * | 7/2001 | Furukawa et al. | 310/313 R |

FOREIGN PATENT DOCUMENTS

| | | |
|---|---|---|
| DE | 198 30 559 | 1/2000 |
| WO | WO 99/56829 | 11/1999 |

* cited by examiner

*Primary Examiner*—George Manuel
(74) *Attorney, Agent, or Firm*—Barnes & Thornburg LLP

(57) ABSTRACT

The invention relates to a physically active patch having a planar substrate which is provided on one side with an adhesive layer, a first electrode being arranged, at least in regions, on the side of the substrate remote from the adhesive layer, then above said electrode, at least in regions, a layer formed from a piezoelectric, quasi-piezoelectric and/or electro-strictive polymer material, and above same, at least in regions, a second electrode.

26 Claims, 3 Drawing Sheets

PHYSICALLY ACTIVE PATCH, METHODS OF MANUFACTURING SAME AND ITS USE

Figure 1:
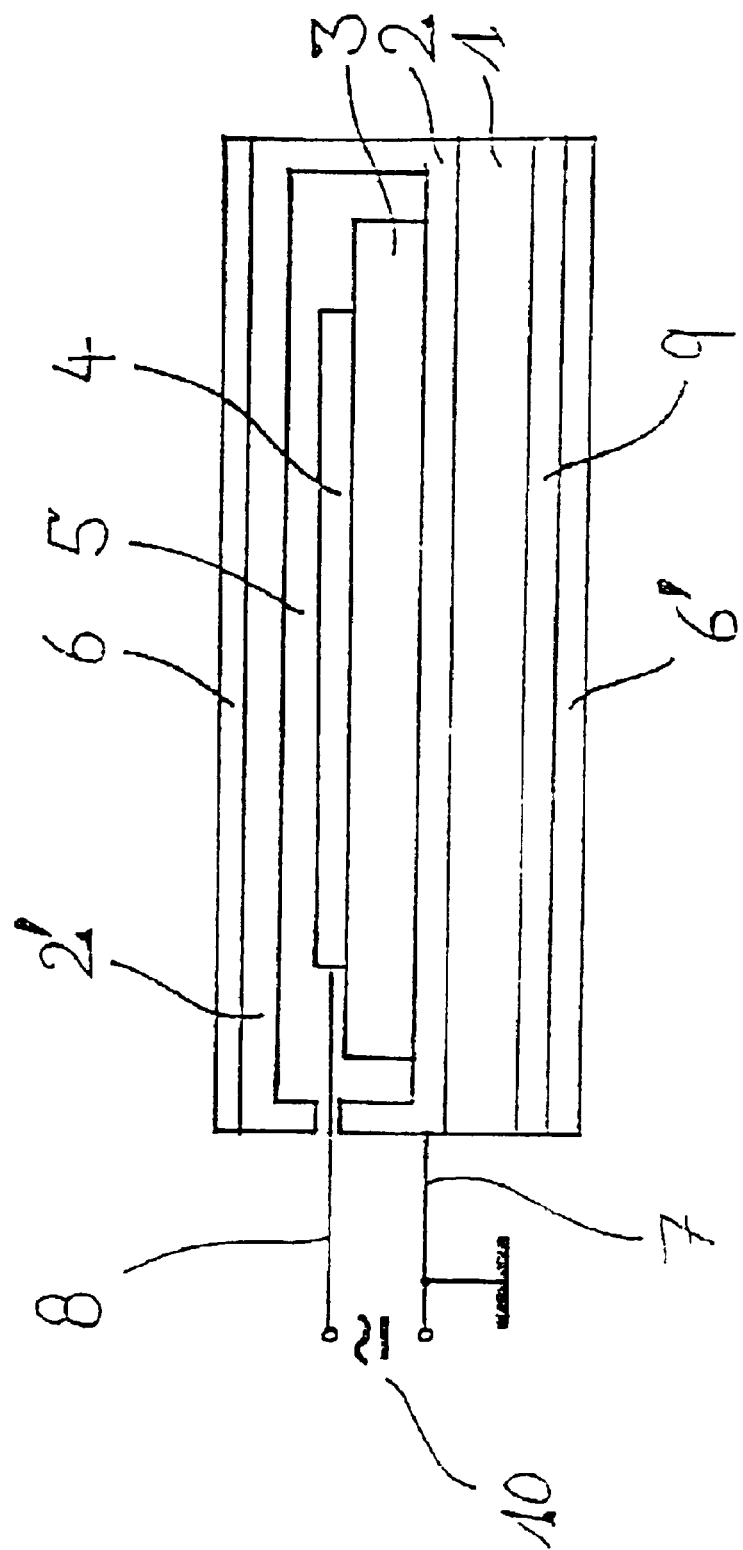

The present invention relates to a physically active patch, methods of manufacturing same and the use thereof.

Physically active patches of this type can be used in the domain of human and veterinary medicine, especially for the alleviation of diseases, for pain relief, for prophylactic care of the body and health, and for improving the fitness of humans and animals and also for cosmetic applications.

Functional patches are already prior art. They are used in human medicine. They include pain-relief and analgesic patches, patches for labour and for scars, hormone and temperature patches or even patches to counteract nausea. These functional patches have a common principle of action: the active substance (medicament) is dissolved for example in a gel. This gel is located in a reservoir above a permeable membrane through which it can continuously diffuse. Additional active substances contained in the gel ensure that the medicament reaches the uppermost layers of the skin. Blood vessels lying below same absorb the active substance and it is then transported into the body. As an example can be mentioned the Schmerzpflaster (=anti-pain patch) Durgesic produced by the Janssen Company, in which the active substance fentanyl is applied in a patch reservoir (Durgesic Schmerzpflaster, http://www.janssenpharmaceutica.be/pmp). The patches listed operate according to the principle of diffusion and an active substance is always required. What is disadvantageous about these patches is that they cannot be used with many patients who cannot tolerate the corresponding active substances or are allergic to same. Furthermore, these patches are in many cases very expensive because the active substances comprise complicated pharmaceuticals. What is also disadvantageous is the limited field of application and the fact that they can only be used once.

In addition to this, a functional patch is known (Pain T.E.M.) which operates with micro-current membranes (Pain T.E.M. für Schmerzbekämpfung ohne Medikamente [=for pain relief without medicaments], http://www.schmerzpflaster.at). This is an electrically acting patch, in which micro-currents in the micro-ampere range are passed into the skin. It is used mainly for pain relief and in the case of inflammation. What is disadvantageous about this patch is that in many patients its action does not take place, and if it does take place, is not sufficient.

Furthermore, patches are known which act according to the principle of transcutaneous electric nerve stimulation and are intended to act as pain relief (Transkutane Elektrische Nervenstimulation, http://www.eurovation.de/inhalt/tens.htm) or act as electronic muscle stimulators (Gymform Plus, Electronic Muscle Stimulator, http://www.livwell.com/gymform.htm). These patches are based on the coupling of electrical signals into the skin or muscles. Their effect is very limited and in the case of the muscle stimulators their use is intended for muscle training.

The object of the present invention is to make available a medical patch with which an electromechanical action can be exerted on a human or an animal. The object here is to quote a patch which can be used as often as desired and which has high medical effect, and manufacturing methods and uses of this patch.

This object is accomplished by the physically active patch according to patent claim 1, a method for operating such a patch according to patent claim 19, the use of same according to patent claim 23, and manufacturing methods for such patches according to patent claim 25. The advantageous development of the patch according to the invention and of the methods and use according to the invention are given in the respective dependent claims.

According to the invention, a physically active patch has a substrate which can be secured via an adhesive layer on its one side to the skin of a patient. On the other side is located a piezoelectric, quasi-piezoelectric and/or electrostrictive polymer material embedded between two electrodes.

Depending on the application, polymer materials which can be considered here are piezoelectric vinylidene fluoride homopolymers and copolymers, piezoelectric and quasi-piezoelectric porous polymer materials, e.g. based on polytetrafluoroethylene, polypropylene, polyaryl sulphones, polyether sulphones, polyurethanes, polyesters, cellulose and cellulose derivatives, polyether imides, polyetherether ketones, polyimides, polycarbonates, polybenzimidazoles, polyamides, polyacrylonitriles, tetrafluoroethylene copolymers, polyphenyl sulphide, polystyrene and electrostrictive polymers such as, for example, elastic polymer materials and/or also polymer gels with electrostriction which is above average in strength.

The polymer membrane can be used here in the form of films and/or thin layers or be applied to the substrate.

By comparison with conventional functional patches, the physically active patches according to the invention are distinguished by a considerably improved medical effect. In particular, the patches according to the invention exhibit a clearly quicker and greatly improved medical effect in the case of circulation disorders (e.g. angina pectoris), vein troubles, skin diseases, nervous diseases, back complaints (e.g. disc trouble), tension, dislocations, sprains, arthritis and in the healing of wounds and bones as well as pain relief. The patches according to the invention can be used with great advantage not only in the case of afflictions and illness which have already occurred but they also find positive application in prophylactic health care and in increasing the fitness of the body. A sufficiently good electrical insulation and electromagnetic shielding of the patch prevents any danger from electrical voltage and high-frequency fields in the use of the patch. No allergies occur. The treatment is pain-free. By comparison with conventional therapeutic measures, the patch according to the invention also has the advantage that it is flexible and adapts to body parts of any shape. It can be laid e.g. around the neck or a finger and releases there its therapeutic effect on the basis of its optimal mechanical adaptation and propitious coupling of the mechanical waves and oscillations. Through the structuring of the electrodes of the electrically active polymer element and the manner of application of the electrical voltage (high frequency, frequency in the sound range and d.c. voltage, electrical scanning of the line and matrix structures), a particularly advantageous mechanical stimulation of the skin, and additionally of body parts lying deeper, is realised (depth of action up to several centimeters). Furthermore it is advantageous to apply a mechanical wave or a pressure in the exact spot, by the microstructured matrix electrodes according to the invention being used. In the case of this application it is possible to speak of electromechanical puncture. Furthermore the favourable acoustic impedance of the electrically active polymer materials to be used plays a positive role which largely prevents the reflection of the mechanical oscillations and waves at the surface of the body which would reduce the medical effect. In addition, the patches according to the invention also have cosmetic effects (avoidance and smoothing of wrinkles) and can be used as often as desired.

Some examples of patches according to the invention and their application and manufacture are described below.

Figure 2:
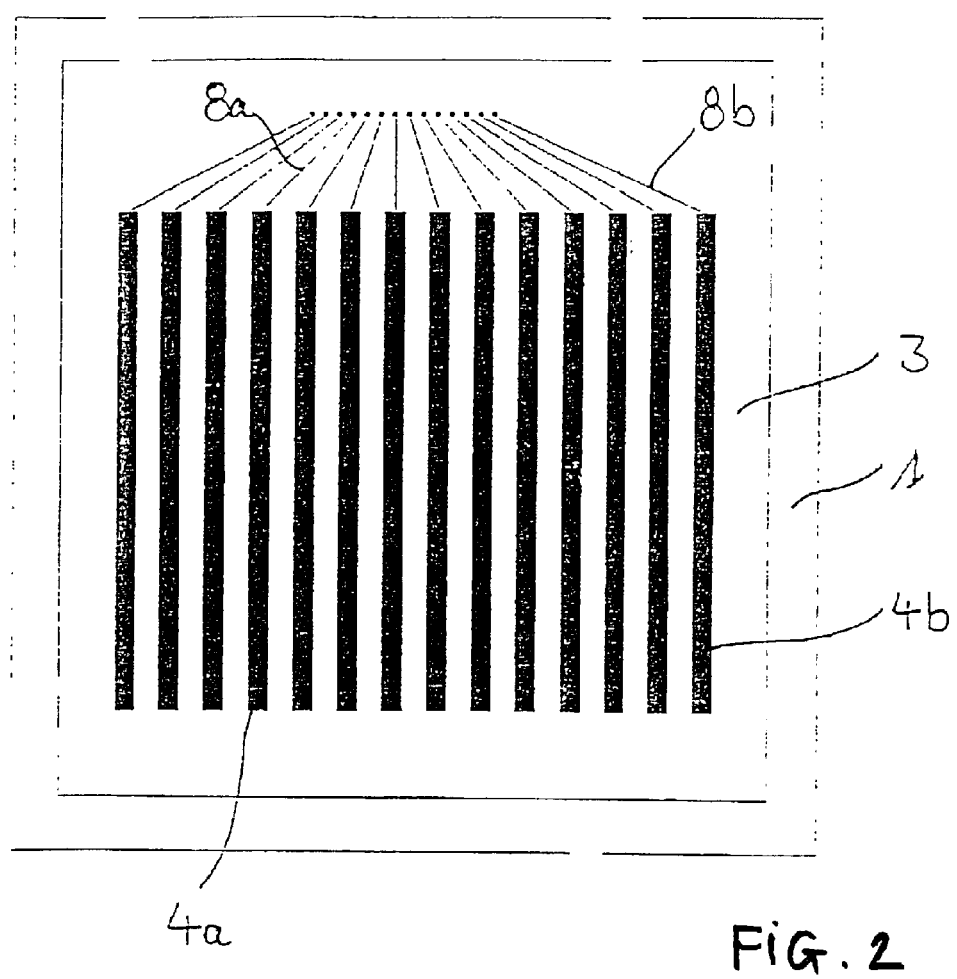

FIG. 1 shows the structure of a patch according to the invention;

FIG. 2 a further patch and

Figure 3:
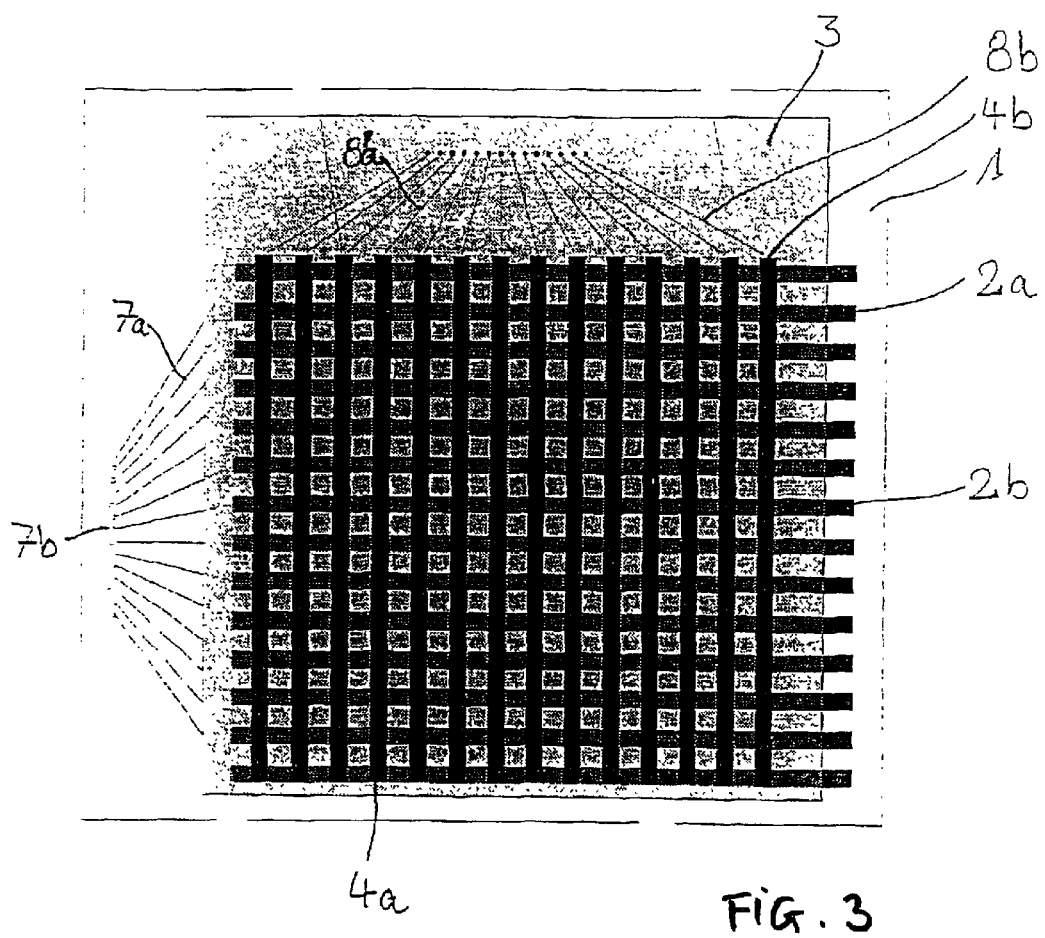

FIG. 3 a further patch according to the invention.

FIG. 1 shows the typical structure of a physically active patch according to the invention. An earthed basic electrode 2, which serves simultaneously as an electromagnetic shield, is applied to an elastomeric film 1 provided with a medically tolerable adhesive layer 9. Then follows a piezoelectric or electrostrictive active polymer layer or film 3, which bears on its upper side a top electrode 4. The polymer layer or film 3 can here be poured or laid onto the electrode 2. Polymer layer 3 and electrode 2 can also be manufactured in advance as a composite in the form of a metallised polymer layer, the metallisation forming the electrode 2. An insulating layer 5, a shielding layer 2 which is connected to the electrode 2 in an electrically conductive manner and forms with said electrode a Faraday cage about layers 3, 4 and 5, and protective layer 6 adjoin upwards and cover the electrodes 2, 4 and the polymer layer 3. Electrical supply lines 7, 8 lead to the electrodes 2, 4. Particular attention is to be paid to the material of the basic electrode 2 acting as an electromagnetic shield and to protective shield 6. In respect of providing an efficient electromagnetic shield, silver and ferromagnetic materials have proved to be advantageous as electrode materials for the basic electrode 2. If an electrical a.c. voltage from a voltage source 10 is applied to the physically active patch or the electrodes 2, 4 via electric supply lines 7 or 8, the electrically active functional element 3 is excited to thickness and longitudinal oscillations which couple via the elastomer film 1 into the human or animal body and in this manner exert a positive medical effect. By additional application of a d.c. voltage, the medical effect of the patch is greatly increased. The frequency of the applied a.c. voltage is, depending on the particular application, in the range between 1 Hz and 10 MHz. The electrical field strengths to be used are 0.1 MV/m to 100 MV/m. The physically active patch has a sufficiently positive medical effect particularly when the piezoelectric and quasi-piezoelectric coefficients of the piezo materials used are at least 30 pC/N or the electrostrictive materials have an electrostriction which leads with the same electrical fields to the same thickness and longitudinal oscillations as in the case of the piezoelectric materials used. The adhesive layer 9 and the shield 2', which itself already represents a protective layer, are for their part covered on their outer sides by protective layers 6' or 6.

In a further variant represented in FIG. 2, the electrodes 3, 4 of the piezoelectrically active layer or foil 3 are structured. When this variant is used, the electrical voltage is applied at intervals of time to the electrodes 4a, 4b which are structured e.g. as lines. Then through the electromechanical effects of the electrically active materials 3, a mechanical travelling wave is produced from one partial electrode to the next partial electrode which is coupled via the skin into the body and exerts a particularly strong therapeutic effect there. The frequency of the travelling wave is between 0.1 Hz and 1 MHz. Due to the line structure of the electrodes 4a, 4b of the electrically active element, it is also possible to apply locally selective mechanical waves and deformations to the body.

Through the use of microelectronic technologies, therefore, in a further variant, matrix-form electrode structures 4a, 4b, 2a, 2b can be realised and electrically triggered. This is represented in FIG. 3, each electrode 2, 4 having stepped partial electrodes 2a, 2b or 4a, 4b running parallel to one another and able to be controlled separately from one another. The partial electrodes of the two electrodes 2, 4 are here disposed at right angles to one another and together form a matrix arrangement. Thus it is possible to realise a locally defined electromechanical stimulation also in micrometer ranges (e.g. 100×100 µm) with suitable dimensioning of the step width of the partial electrodes on the parts of the body to be treated. For the use of the patches according to the invention, constant voltage sources and/or high-frequency generators are required besides the necessary amplifiers, which are accommodated for example, and advantageously for the user of the patches, in mobile telephones. Thus it is possible to realise a mobile use of the patches according to the invention.

Electrodes of this type, represented in FIGS. 1 to 3, can be produced as follows:

1. To produce a physically active patch according to the invention, silver is applied as a basic electrode, by vapour disposition in a high vacuum, to an elastomeric film with a thickness of 30 µm which is provided on one side with an adhesive layer. Thereafter an organosoluble vinylidene fluoride trifluoroethylene copolymer is used which is dissolved in a 10% by weight solution in methyl ethyl ketone and the polymer solution is centrifuged onto the basic electrode. After a drying process, a fluoropolymer layer is produced with a thickness of 20 µm, which is piezoelectrically activated by an electrical polarisation process with electrical field strengths of at least 200 MV/m and thus a piezoelectric coefficient of 30 pC/N is produced in the polymer layer. Thereafter follow the application of the top electrode, the application of an insulating layer formed from a silicone or polyurethane polymer and, after contacting of the electrical supply lines, the electromagnetic shield. Instead of the electrically polarised vinylidene fluoride trifluoroethylene copolymer layer, piezoelectric or quasi-piezoelectric electret foils formed from porous polymer material can be used, for example based on polytetrafluoroethylene, polypropylene, polystyrene or polyether sulphone which have a piezoelectric coefficient of at least 30 pC/N and which are distinguished in addition by a permanent electrical charge. Due to the additional electrical charge, the electret foil enters an electrostatic bonding with the elastomeric film vapour-deposited on one side and forms a solid bond with it. Alternatively, the electret foil can also be glued to the elastomeric film. To operate the physically active patch, a high-frequency voltage of 1 MHz and 10 V is used, which is applied after the patch has been stuck onto the part of the body to be treated. According to the type of treatment, the voltage is applied for between 10 seconds and 10 hours with up to 10 repetitions.

2. For treating back pain, two physically active patches are stuck onto the back, parallel to and on both sides of the spine. The piezoelectrically active polymer elements of the patches here have line electrode structures disposed perpendicular to the spine with a width of 1 cm, length of 10 cm and at a spacing of 1 cm. For treating pain, a high-frequency voltage of 1 MHz is applied for ten minutes at intervals of time to the line electrodes. With a clock frequency of 1 kHz, the individual line electrodes are triggered chronologically in succession and repeatedly. By this means a type of electromechanical travelling wave spreads along the electrodes and causes a specific mechanical stimulation of the part of the back, with a strongly pain-reducing effect.

3. For smoothing wrinkles, e.g. on the forehead, an electrostrictive rubber film is used, which is metallised on both sides and has a thickness of 30 µm, and it is integrated into the physically active patch. This smoothing of the skin takes place by the 100 V d.c. voltage pulses with a clock frequency of 1 Hz being applied for 5 min. Due to the electrostriction of the rubber film, the physically active patch, which is securely connected to the skin, stretches and exercises a wrinkle-smoothing effect. This patch can also be used to prevent wrinkles.

4. To stimulate the foot reflex zones, a physically active patch is stuck to the sole of the right or left foot. The patch is here adapted to the shape of the sole. The physically active element comprises a piezoelectric foil which has a structured electrode which images the foot reflex zones, and foil and electrode can be electrically triggered individually or in combination. To stimulate the foot reflexes, a high frequency of approx. 10 MHz is applied to the electrode, as a sequel to which an ultrasound wave is generated which extends locally in the sole and in this way stimulates the foot reflexes and exerts its therapeutic effect on the body.

5. To an earlobe is applied a patch measuring approx. 2 mm×5 mm which is provided with microplugs and microcontacts. As the active element is used here a piezoelectric polymer layer or film which has a matrix-form electrode structure with e.g. 50×50 elements. Thus it is possible to cause microscopically exact and localised electromechanical stimuli to act on the skin and the body by applying to the matrix elements electrical pulses with a length of e.g. 10 ms and a frequency of 1 kHz and a peak voltage of 100 V. elements. The therapeutic treatment takes place either by a selected matrix element being triggered or by the entire matrix being scanned. The treatment time is between 30 s and 300 s. The pulse-shaped electrical stimulation causes, on the surface of the earlobe, locally selective pinprick-like mechanical impulses which penetrate deep into the earlobe and exert their stimulating positive effect there (electromechanical puncture.)

What is claimed is:

1. A physically active patch having a planar substrate which is provided on one side with an adhesive layer, and a side remote from the adhesive layer, the side of the substrate remote from the adhesive layer including at least in regions a first electrode and above the first electrode, at least in regions, a layer including at least one of a piezoelectric polymer material, a quasi-piezoelectric polymer material and an electrostrictive polymer material, and above the at least one of a piezoelectric polymer material, a quasi-piezoelectric polymer material and an electrostrictive polymer material, at least in regions, a second electrode, the first electrode and the second electrodes are structured, having a plurality of individual electrode strips lying parallel to one another, the two electrodes being so disposed that a longitudinal direction of the electrode strips of the first electrode is perpendicular to a longitudinal direction of the electrode strips of the second electrode.

2. The patch of claim 1 wherein the layer formed from at least one of a piezoelectric polymer material, a quasi-piezoelectric polymer material and an electrostrictive polymer material is at least one of a foil and a thin film.

3. The patch of claim 1 wherein the layer formed from at least one of a piezoelectric polymer material, a quasi-piezoelectric polymer material and an electrostrictive polymer material contains at least one of: piezoelectric vinylidene fluoride homopolymers, piezoelectric vinylidene fluoride copolymers, piezoelectric porous polymer materials, and quasi-piezoelectric porous polymer materials based on at least one of polytetrafluoroethylene, polypropylene, polyaryl sulphones, polyether sulphones, polyurethanes, polyesters, cellulose, cellulose derivatives, polyether imides, polyetherether ketones, polyimides, polycarbonates, polybenzimadazoles, polyamides, polyacrylonitriles, terafluoroethylene copolymers, polyphenyl sulphide, polystyrene, electrostrictive polymers, electrostrictive elastic polymer materials and electrostrictive polymer gels.

4. The patch of claim 1 wherein the at least one of a piezoelectric polymer material and a quasi-piezoelectric polymer material has a piezoelectric or quasi-piezoelectric coefficient of at least 30 pC/N.

5. The patch of claim 1 wherein the substrate is an elastomeric film.

6. The patch of claim 1 wherein the adhesive layer contains an adhesive.

7. The patch of claim 1 wherein the first electrode is earthed.

8. The patch of claim 1 wherein the first electrode contains at least one of silver and ferromagnetic materials.

9. The patch of claim 1 wherein at least one of the layer formed from at least one of a piezoelectric polymer material, a quasi-piezoelectric polymer material and an electrostrictive polymer material and the second electrode is electrically insulated by an electrical insulating layer.

10. The patch of claim 9 wherein the insulating layer contains at least one of a silicone and polyurethane polymer.

11. The patch of claim 1 wherein at least one of the layer formed from at least one of a piezoelectric polymer material, a quasi-piezoelectric polymer material and an electrostrictive polymer material, the second electrode and the electrical insulating layer is protected by at least one of an electromagnetic shielding layer and a protective layer.

12. The patch of claim 11 wherein the at least one of the layer formed from at least one of a piezoelectric polymer material, a quasi-piezoelectric polymer material and an electrostrictive polymer material, the second electrode and the electrical insulating layer is protected by a layer which is both a protective layer and an electromagnetic shield.

13. The patch of claim 11 wherein the at least one of the electromagnetic shielding layer and the protective layer is electrically connected to the first electrode.

14. The patch of claim 11 wherein the first electrode and the at least one of the electromagnetic shielding layer and the protective layer form a Faraday cage for at least one of the layer formed from at least one of a piezoelectric polymer material, a quasi-piezoelectric polymer material and an electrostrictive polymer material, the second electrode and the electrical insulating layer.

15. The patch of claim 11 wherein at least one of the first electrode and the second electrode has a plurality of individual, strip-shaped electrode strips lying parallel to one another.

16. The patch of claim 1 further including a voltage source to which the first and the second electrodes are connected.

17. The patch of claim 16 wherein the voltage source is one of a constant voltage supply and a high-frequency voltage supply.

18. The patch of claim 16 connected to a mobile telephone, the voltage source being arranged in the mobile telephone.

19. A method for operating a patch according to claim 1 including applying an a.c. voltage to the first and second electrodes.

20. The method of claim 19 wherein the a.c. voltage has a frequency between 1 Hz and 10 MHz.

21. The method of claim 19 wherein the a.c. voltage generates between the two electrodes an electric field strength of between 0.1 MV/m and 100 MV/m.

22. The method of claim 19 further including applying a d.c. voltage to the electrodes.

23. Use of the patch of claim 1 in one of human medicine, veterinary medicine and cosmetics.

24. The use of claim 23 for one of the alleviation of disease, for pain relief, for prophylactic care of the body, for improving the fitness of a human being, for improving the fitness of an animal, for avoiding wrinkles and for smoothing out wrinkles.

25. A patch according to claim 1 comprising a) an elastomeric film vapor-deposited with a first electrode by means of a vacuum method, b) an organosoluble polymer solution centrifuged onto the first electrode and dried to form a polymer layer, c) the polymer layer piezoelectrically activated by the application of a voltage, d) the second electrode applied to the polymer layer, e) the electrodes contacted with supply lines and f) a protective layer providing an electromagnetic shield applied to the insulating layer.

26. The patch of claim 25 wherein a) the elastomeric film comprises a vacuum vapor-deposited silver layer as said first electrode, and b) the oraganosoluble polymer solution centrifuged onto the first electrode and dried to form a polymer layer comprises an organosoluble vinylidene fluoride trifluoroethyl copolymer dissolved in a 10% by weight solution in methyl ethyl ketone and centrifuged onto the first electrode and dried.

* * * * *